US000001511H

United States Statutory Invention Registration [19]

[11] Reg. Number: H1511

Chappell et al.

[45] Published: Dec. 5, 1995

[54] ABSORBENT ARTICLES HAVING IMPROVED LONGITUDINAL FLUID MOVEMENT

[76] Inventors: Charles W. Chappell, 8599 Le Sourdsville Rd., P.O. Box 278, West Chester, Ohio 45071; Lee M. Hines, 320 E. Mills Ave., Cincinnati, Ohio 45215; John L. Hammons, 7379 Dust Commander Ct., Hamilton, Ohio 45011; Theresa L. Johnson, 11785 Rose La. #C, Cincinnati, Ohio 45246

[21] Appl. No.: 943,256

[22] Filed: Sep. 10, 1992

[51] Int. Cl.[6] ..... A61F 13/15; A61F 13/54

[52] U.S. Cl. ..... 604/383; 604/367; 604/378; 604/384; 604/385.1

[58] Field of Search ..... 604/367, 368, 604/378, 380, 384, 385.1, 383

[56] References Cited

U.S. PATENT DOCUMENTS

| | | | |
|---|---|---|---|
| 810,132 | 1/1906 | Green . | |
| 2,896,618 | 7/1959 | Schaefer | 128/156 |
| 3,211,147 | 10/1965 | Pherson et al. | 128/284 |
| 3,343,543 | 9/1967 | Glassman | 604/380 |
| 3,375,827 | 4/1968 | Bletzinger et al. | 604/380 |
| 3,667,468 | 6/1972 | Nystrand et al. | 604/380 |
| 3,731,686 | 5/1973 | Chatterjee | 128/285 |
| 3,766,922 | 10/1973 | Krusko | 128/284 |
| 3,965,904 | 6/1976 | Mesek et al. | 128/284 |
| 3,971,381 | 7/1976 | Gibson | 128/296 |
| 4,041,950 | 8/1977 | Jones, Sr. | 128/287 |
| 4,259,958 | 4/1981 | Goodbar | 604/380 X |
| 4,372,312 | 2/1983 | Fendler et al. | 128/290 R |
| 4,546,027 | 10/1985 | Holvoet et al. | 428/109 |
| 4,559,050 | 12/1985 | Iskra | 604/368 |
| 4,578,070 | 3/1986 | Holtman | 604/378 |
| 4,681,577 | 7/1987 | Stern et al. | 604/380 X |
| 4,685,914 | 8/1987 | Holtman | 604/368 |
| 4,723,954 | 2/1988 | Pieniak | 604/384 |
| 4,738,675 | 4/1988 | Buckley et al. | 604/380 |
| 4,758,240 | 7/1988 | Glassman | 604/379 |
| 4,758,241 | 7/1988 | Papajohn | 604/387 |
| 4,775,375 | 10/1988 | Aledo | 604/378 |
| 4,781,710 | 11/1988 | Megison et al. | 604/378 |
| 4,908,026 | 3/1990 | Sukiennik et al. | 604/378 |
| 4,973,325 | 11/1990 | Sherrod et al. | 604/368 |
| 4,988,344 | 1/1991 | Reising et al. | 604/380 X |
| 5,149,332 | 9/1992 | Walton et al. | 604/380 X |

FOREIGN PATENT DOCUMENTS

| | | | |
|---|---|---|---|
| 0122803A2 | 10/1984 | European Pat. Off. | A61F 5/44 |
| 0146190A2 | 12/1984 | European Pat. Off. | A61F 13/18 |
| 0140470A1 | 5/1985 | European Pat. Off. | A61F 5/44 |
| 0159671A2 | 10/1985 | European Pat. Off. | A61F 13/18 |
| 0316771A2 | 5/1989 | European Pat. Off. | A61F 13/18 |
| 032198A2 | 6/1989 | European Pat. Off. | A61F 5/44 |
| 0359391A1 | 3/1990 | European Pat. Off. | A61F 13/15 |
| 0397110A2 | 11/1990 | European Pat. Off. | A61F 13/46 |
| 0471114A2 | 2/1992 | European Pat. Off. | A61F 13/15 |
| 0470392A1 | 2/1992 | European Pat. Off. | A61F 13/46 |

(List continued on next page.)

*Primary Examiner*—Charles T. Jordan
*Assistant Examiner*—Theresa M. Wesson

[57] ABSTRACT

The present invention provides absorbent articles, especially sanitary napkins, containing a flow regulator positioned between the topsheet and the absorbent core. In-use, fluid deposited on the topsheet is internally moved in the longitudinal direction by the flow regulator before being released to the absorbent core. By moving substantial amounts of fluid in the longitudinal direction the flow regulator provides a more effective use of the absorbent core.

19 Claims, 4 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

FOREIGN PATENT DOCUMENTS

| | | | |
|---|---|---|---|
| 0481322A1 | 4/1992 | European Pat. Off. | A61F 13/48 |
| 3301555 | 8/1984 | Germany . | |
| 8005-148 | 7/1980 | Sweden | A41B 13/02 |
| 8105-800 | 10/1981 | Sweden | A41B 13/02 |
| 2097722A | 11/1982 | United Kingdom | B32B 3/12 |
| 2100130A | 12/1982 | United Kingdom | A41B 13/02 |
| WO82/01991 | 6/1982 | WIPO | A61G 7/04 |
| WO8700-057-A | 6/1985 | WIPO | A41B 13/02 |
| WO86/01378 | 3/1986 | WIPO | A41B 13/02 |
| WO86/02543 | 5/1986 | WIPO | A61F 13/16 |
| WO91/11161 | 8/1991 | WIPO | A61F 13/15 |

ABSORBENT ARTICLES HAVING IMPROVED LONGITUDINAL FLUID MOVEMENT

TECHNICAL FIELD

The present invention relates to absorbent articles especially catamenial articles such as sanitary napkins. Such articles are especially adapted for absorbing various body fluids, especially menses, while providing comfort and fit to the wearer.

BACKGROUND OF THE INVENTION

A wide variety of structures for disposable absorbent articles to collect body fluids are known in the art. Commercial absorbent articles include diapers, adult incontinence products, catamenials and bandages. Disposable products of this type comprise some functional members for receiving, absorbing and retaining fluids. Generally, such absorbent articles contain a core of absorbent materials mainly comprising fibrous cellulose. Typically, such articles include a fluid-permeable topsheet, an absorbent core and a fluid-impermeable backsheet.

In the case of catamenial pads, women have come to expect a high level of performance in terms of comfort and fit, retention of fluid, and minimal staining. Above all, leakage of fluid from the pad onto undergarments is regarded as totally unacceptable.

Improving the performance of sanitary napkins continues to be a formidable undertaking, although a number of improvements have been made in both their materials and structures. However, eliminating leakage, particularly along the inside of the thighs, without compromising fit and comfort, has not met the desired needs of the consumer.

Leakage from sanitary napkins is generally attributed to a high concentration of fluid at the point where the menses exits the body and immediately contacts the surface of the napkin. At this point of deposit, the napkin's absorbent material quickly becomes super-saturated. The menses migrates radially from this point and leaks from the sides nearest the wearer's legs. This often results in the smearing of menses on the body and soiling of the undergarments. Attempts to eliminate leakage include: construction of a densified edge to hold the fluid back (U.S. Pat. No. 4,820,295, Chapas et al, issued Apr. 11, 1989); barrier sheets surrounding the article (U.S. Pat. No. 4,666,439, Williams et al, issued May 19, 1987); and "winged" side edges which wrap around the panties (U.S. Pat. No. 4,701,177, Ellis et al, issued Oct. 10, 1987, incorporated herein by reference).

Unfortunately, overdensifying sections of the sanitary napkins detracts from comfort, in-use. Some users are not attracted to the "winged" product, and others are not satisfied with the barrier product. However, since a large part of most absorbent articles remains relatively dry and not utilized, it has now been determined that providing a means to direct fluid from the point of deposit to the areas of the article not fully utilized will avoid super-saturation and considerably reduce or eliminate leakage.

Apart from undergarment soiling, the user of modern sanitary napkins, and the like, has come to expect that the surface of such articles will provide a cleaner, more sanitary and drier aspect than common cloth or nonwoven materials have historically provided. Thus, modern sanitary napkins, diapers and incontinence devices are typically provided with topsheets that are designed to move fluids rapidly through said topsheets and into an underlying absorbent core for storage. As can be envisaged, the more rapid and thorough this movement, the drier and cleaner the surface of the article.

Stated succinctly, the present invention not only provides the desired, directional movement of fluids noted above, which allows improved use of the overall absorbent capacity of the article and less side-leakage, but also provides means to draw fluids through the topsheet, thereby enhancing the desired dry, sanitary benefits, in-use.

Furthermore, the articles which employ the technology embodied in the present invention are more comfortable and better fitting than articles which rely, for example, on highly dense absorbent core regions to achieve fluid movement. Stated otherwise, the technology herein achieves the fluid directionality and handling characteristics available from dense, but uncomfortable, cores in a soft, pliable, low-density and comfortable pad.

SUMMARY OF THE INVENTION

The present invention pertains, in a preferred embodiment, to absorbent articles, preferably a sanitary napkin or pantiliner, but also includes diapers, adult incontinence garments, bandages, and the like. The absorbent article has a longitudinal direction, a transverse direction, and a z-direction. The absorbent article includes a fluid pervious topsheet and a fluid impervious backsheet joined to the topsheet. An absorbent core is positioned between the topsheet and the backsheet. The core has an uppermost surface facing topsheet and a lowermost surface facing the backsheet. A flow regulator is positioned between the topsheet and the absorbent core. The flow regulator enhances movement of fluid in the longitudinal direction while controlling movement of fluid in the transverse and z-directions.

In a preferred embodiment the flow regulator comprises a secondary topsheet and a plurality of fibers having external capillary channels. Preferably, the secondary topsheet is arranged in a plurality of pleats extending substantially parallel to the longitudinal direction of the absorbent article. The fibers having external capillary channels are formed into a yarn and positioned within the pleats of the secondary topsheet. The yarn of fibers positioned within the pleats of the secondary topsheet is twisted.

In another preferred embodiment, the fibers having external capillary channels are formed into a nonwoven. The nonwoven comprised of fibers having external capillary channels is superposed upon the secondary topsheet. The fibers having external capillary channels of the nonwoven are preferably oriented such that their channels lie substantially parallel to the longitudinal direction of the article. Preferably, the fibers having external capillary channels are hydrophilic. Preferably, the capillary channel fibers have a "H"-shaped cross-section.

BRIEF DESCRIPTION OF THE DRAWINGS

While the specification concludes with claims particularly pointing out and distinctly claiming the present invention, it is believed that the present invention will be better understood from the following description in conjunction with the accompanying drawings, in which like reference numbers identify identical elements and wherein;

DETAILED DESCRIPTION OF THE INVENTION

1. General Description of the Absorbent Article

As used herein, the term "absorbent article" refers to devices which absorb and contain body exudates, and, more specifically, refers to devices which are placed against or in proximity to the body of the wearer to absorb and contain the various exudates discharged from the body. The term "absorbent article" is intended to include diapers, catamenial pads, sanitary napkins, pantiliners, incontinent pads, and the like. The term "disposable" is used herein to describe absorbent articles which are not intended to be laundered or otherwise restored or reused as an absorbent article (i.e., they are intended to be discarded after a single use, and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and pad.

Figure 1:
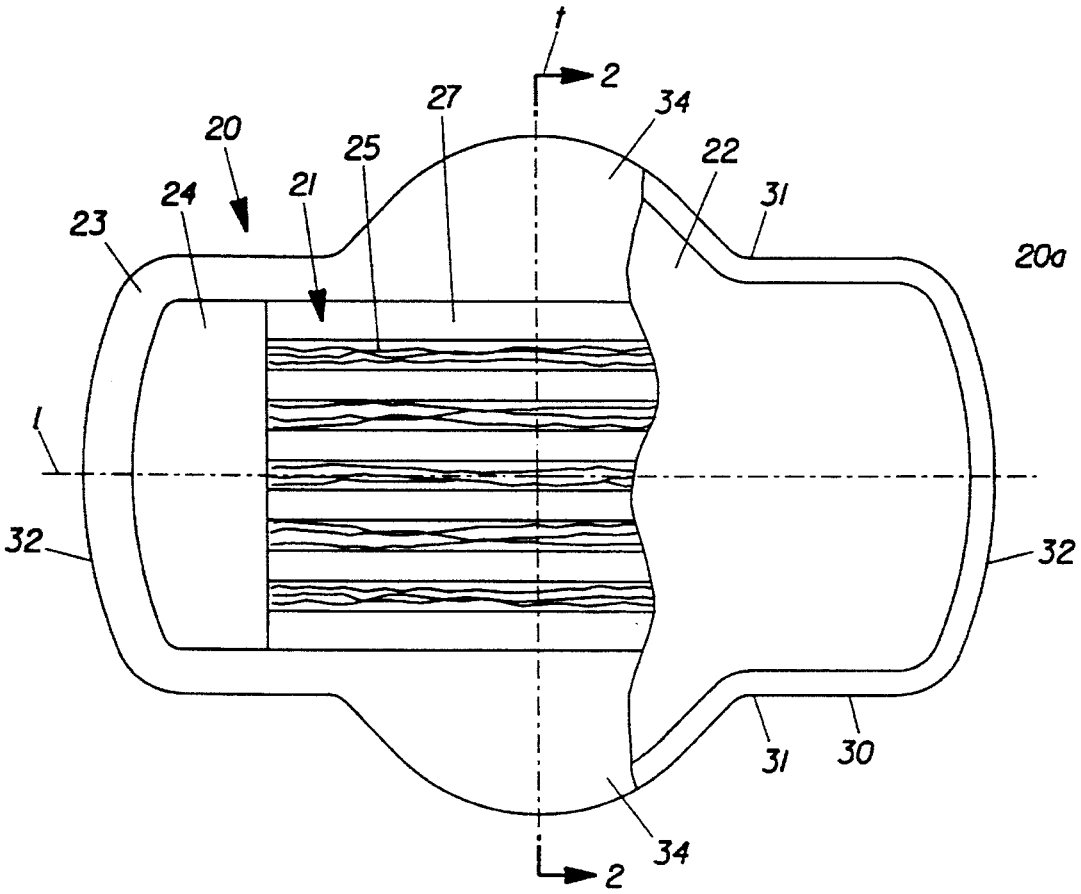
FIG. 1 is a top plan view of a preferred sanitary napkin of the present invention with portions cut-away to more clearly show the construction of the sanitary napkin.

A preferred embodiment of a unitary disposable absorbent article of the present invention is the catamenial pad, sanitary napkin 20, shown in FIG. 1. As used herein, the term "sanitary napkin" refers to an absorbent article which is worn by females adjacent to the pudendal region, generally external to the urogenital region, and which is intended to absorb and contain menstrual fluids and other vaginal discharges from the wearer's body (e.g., blood, menses, and urine). Interlabial devices which reside partially within and partially external of the wearer's vestibule are also within the scope of this invention. As used herein, the term "pudendal" refers to the externally visible female genitalia. It should be understood, however, that the present invention is also applicable to other feminine hygiene or catamenial pads such as pantiliners, or other absorbent articles such as incontinence pads, and the like.

The sanitary napkin 20 has two surfaces, a body-contacting surface or "body surface" 20*a* and a garment surface 20*b*. The sanitary napkin 20 is shown in FIG. 1 as viewed from its body surface 20*a*. The body surface 20*a* is intended to be worn adjacent to the body of the wearer. The garment surface 20*b* of the sanitary napkin 20 (shown in FIG. 2) is on the opposite side and is intended to be placed adjacent to the wearer's undergarments when the sanitary napkin 20 is worn.

The sanitary napkin 20 has two centerlines, a longitudinal centerline "l" and a transverse centerline "t". The term "longitudinal", as used herein, refers to a line, axis or direction in the plane of the sanitary napkin 20 that is generally aligned with (e.g., approximately parallel to) a vertical plane which bisects a standing wearer into left and right body halves when the sanitary napkin 20 is worn. The terms "transverse" or "lateral" as used herein, are interchangeable, and refer to a line, axis or direction which lies within the plane of the sanitary napkin 20 that is generally perpendicular to the longitudinal direction.

FIG. 1 is a top plan view of the sanitary napkin 20 of the present invention in its flat-out state with portions of the structure being cut-away to more clearly show the construction of the sanitary napkin 20 and with the portion of the sanitary napkin 20 which faces or contacts the wearer 20*a*, oriented towards the viewer. As shown in FIG. 1, the sanitary napkin 20 preferably comprises a liquid pervious topsheet 22, a liquid impervious backsheet 23 joined with the topsheet 22, an absorbent core 24 positioned between the topsheet 22 and the backsheet 23, and a flow regulator 21 positioned between the topsheet 22 and the absorbent core 24.

FIG. 1 also shows that the sanitary napkin 20 has a periphery 30 which is defined by the outer edges of the sanitary napkin 20 in which the longitudinal edges (or "side edges") are designated 31 and the end edges (or "ends") are designated 32.

Sanitary napkin 20 preferably includes optional side flaps or "wings" 34 that are folded around the crotch portion of the wearer's panties. The side flaps 34 can serve a number of purposes, including, but not limited to protecting the wearer's panties from soiling and keeping the sanitary napkin secured to the wearer's panties.

Figure 2:
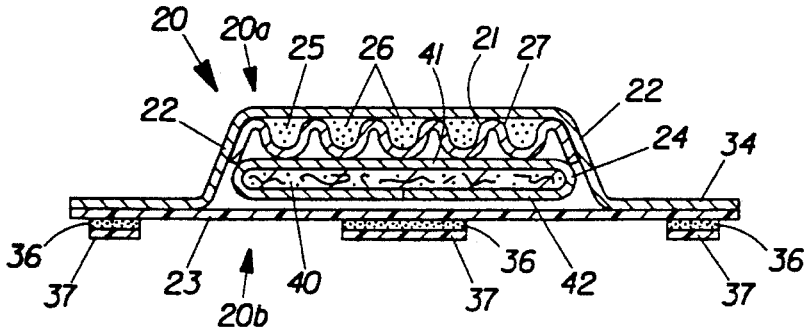
FIG. 2 is a cross-sectional view of the sanitary napkin of FIG. 1 taken along line 2—2.

FIG. 2 is a cross-sectional view of the sanitary napkin 20 taken along section line 2—2 of FIG. 1. As can be seen in FIG. 2, the flow regulator 21 preferably comprises a secondary topsheet 27 and a plurality of fibers 25 having external capillary channels. The secondary topsheet 27 preferably includes plurality of pleats 26 extending substantially parallel to the longitudinal direction of the sanitary napkin 20. The fibers 25 having external capillary channels are preferably positioned within pleats 26 of the secondary topsheet 27.

The sanitary napkin 20 preferably includes an adhesive fastening means 36 for attaching the sanitary napkin 20 to the undergarment of the wearer. Removable release liners 37 cover the adhesive fastening means 36 to keep the adhesive from sticking to a surface other than the crotch portion of the undergarment prior to use.

In addition to having a longitudinal direction and a transverse direction, the sanitary napkin 20 also a "z" direction or axis, which is the direction proceeding down through the topsheet 22 and into whatever fluid storage core 24 that may be provided. The objective is to provide a gradient of capillary suction between the topsheet 22 and underlying layer or layers of the articles herein, such that fluid is eventually drawn in the "z" direction and away from the topsheet of the article into its ultimate storage layer.

By employing a flow regulator which preferably comprises a secondary topsheet arranged in a plurality of longitudinal pleats in which is positioned a plurality of fibers having external capillary channels, fluid flow in the longitudinal direction is promoted, which enhances the overall useful absorbency of the article. Moreover, fluid flow in the transverse direction is controlled, thereby minimizing, or even entirely avoiding, leakage of fluid around the lateral edges of the article. Thus, unlike absorbent articles of the prior art which move fluids in an undirected manner in the x, y and z directions by means of fibrous batts which comprise inter-fiber capillary voids, the flow regulator herein can be used to provide desirable fluid directionality. Thus, it will be appreciated that the absorbent articles of this invention function in a substantially different way, using substantially different materials to provide substantially different benefits than the various art-disclosed absorbent structures which do not employ a flow regulator preferably comprised of a secondary topsheet and fibers having external intrafiber capillary channels to promote the passage of bodily fluids in the longitudinal direction.

The individual components of the sanitary napkin will now be looked at in greater detail.

2. Individual Components of the Sanitary Napkin

A. The Topsheet

The topsheet 22 is compliant, soft feeling, and non-irritating to the wearer's skin. Further, the topsheet 22 is liquid pervious permitting liquids (e.g., menses and/or urine) to readily penetrate through its thickness. A suitable topsheet 22 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers.

A preferred topsheet 22 comprises an apertured formed film. Apertured formed films are preferred for the topsheet because they are pervious to body exudates and yet non-absorbent and have a reduced tendency to allow liquids to pass back through and rewet the wearer's skin. Thus, the surface of the formed film which is in contact with the body remains dry, thereby reducing body soiling and creating a more comfortable feel for the wearer. Suitable formed films are described in U.S. Pat. No. 3,929,135 issued to Thompson on Dec. 30, 1975; U.S. Pat. No. 4,324,246 issued to Mullane et al. on Apr. 13, 1982; U.S. Pat. No. 4,342,314 issued to Radel et al. on Aug. 3, 1982; U.S. Pat. No. 4,463,045 issued to Ahr et al. on Jul. 31, 1984; U.S. Pat. No. 4,629,643 issued to Curro et al. on Dec. 16, 1986; and U.S. Pat. No. 5,006,394 issued to Baird on Apr. 9, 1991. Each of these patents are incorporated herein by reference. The preferred topsheet 22 for the present invention is the formed film described in one or more of the above patents and marketed on sanitary napkins by The Procter & Gamble Company of Cincinnati, Ohio as "DRI-WEAVE".

In a preferred embodiment of the present invention, the body surface of the formed film topsheet 22 is hydrophilic so as to help liquid to transfer through the topsheet 22 faster than if the body surface was not hydrophilic. This will diminish the likelihood that menstrual fluid will flow off the topsheet 22 rather than flowing into and being absorbed by the absorbent core 24. In a preferred embodiment, surfactant is incorporated into the polymeric materials of the formed film topsheet 22 such as is described in U.S. patent application Ser. No. 07/794,745 entitled "Absorbent Article Having A Nonwoven and Apertured Film Coversheet" filed on Nov. 19, 1991 by Aziz et al. Alternatively, the body surface of the topsheet 22 can be made hydrophilic by treating it with a surfactant such as is described in U.S. Pat. No. 4,950,264 issued to Osborn on Aug. 21, 1991 and U.S. Pat. No. 5,009,653 issued to Osborn on Apr. 23, 1991 both of which are incorporated herein by reference.

B. The Absorbent Core

The absorbent core 24 may be any absorbent means which is capable of absorbing or retaining liquids (e.g., menses and/or urine). As shown in FIGS. 1 and 2, the absorbent core 24 has a body surface, a garment surface, side edges, and end edges. The absorbent core 24 may be manufactured in wide variety of sizes and shapes (e.g., rectangular, oval, hourglass, dog bone, asymmetric, etc.) and from a wide variety of liquid-absorbent materials commonly used in sanitary napkins and other absorbent articles such as comminuted wood pulp which is generally referred to as airfelt. An example of other suitable absorbent materials include creped cellulose wadding; meltblown polymers including coform; chemically stiffened, modified or cross-linked cellulosic fibers; capillary channel fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combinations of materials, or mixtures of these.

The configuration and construction of the absorbent core 24 may also be varied (e.g., the absorbent core may have varying caliper zones (e.g., profiled so as to be thicker in the center), hydrophilic gradients, superabsorbent gradients, or lower density and lower average basis weight acquisition zones; or may comprise one or more layers or structures). The total absorbent capacity of the absorbent core 24 should, however, be compatible with the design loading and the intended use of the sanitary napkin 20. Further, the size and absorbent capacity of the absorbent core 24 may be varied to accommodate different uses such as incontinence pads, pantiliners, regular sanitary napkins, or overnight sanitary napkins.

Exemplary absorbent structures for use as the absorbent core 24 of the present invention are described in U.S. Pat. No. 4,950,264 issued to Osborn on Aug. 21, 1990; U.S. Pat. No. 4,610,678 issued to Weisman et al. on Sep. 9, 1986; U.S. Pat. No. 4,834,735 issued to Alemany et al. on May 30, 1989; U.S. Pat. No. 5,009,653 issued to Osborne on Apr. 23, 1991; and European Patent Application No. 0 198 683, The Procter & Gamble Company, published Oct. 22, 1986 in the name of Duenk et al. Each of these patents are incorporated herein by reference.

A preferred embodiment of the absorbent core 24 comprises the laminate structure shown in FIG. 2. The laminate is comprised of a layer of superabsorbent polymeric (or absorbent gelling material) and one or more sheets or webs of cross-linked cellulosic fibers. Suitable cross-linked cellulosic fibers for the absorbent core 24 are described in U.S.

Pat. No. 4,888,093 issued to Cook et al. on Dec. 19, 1989; U.S. Pat. No. 4,822,543 issued to Dean et al. on Apr. 18, 1989; U.S. Pat. No. 4,889,595 issued to Schoggen et al. on Dec. 26, 1989; and U.S. Pat. No. 4,898,642 issued to Moore et al. on Feb. 6, 1990; U.S. Pat. No. 4,935,022 issued Jun. 19, 1990 to Lash et al.; EPO Patent Application Publication Nos. 0 427 316 A2 and 0 427 317 A2 published in the name of Herron et al. on May 15, 1991; and EPO Patent Application Publication No. 0 429 112 A2 published in the name of Herron et al. on May 29, 1991 incorporated herein by reference.

The cross-linked cellulosic fibers in the embodiment shown in FIG. 2 comprises a single sheet that wraps the layers of particles of absorbent gelling material 40. The sheet is wrapped so that it appears as having a "c" configuration when viewed from the end. The wrapped sheet forms an upper layer 41 and a lower layer 42. In alternative embodiments, the laminate can be formed in many other manners, such as by providing separate webs of cross-linked cellulosic material (or other absorbent material) for the different layers of the absorbent core laminate other than a single sheet, or by providing it with additional layers.

In this type of core, curled, twisted, preferably chemically stiffened and cross-linked, cellulose fibers are refined to provide fibers which can be used in sheet form as the absorbent core. The preparation of suitable curled, chemically stiffened cellulosic fibers from which one can prepare the refined, curled, chemical stiffened cellulosic fibers used in detail in U.S. Pat. Nos. 4,888,903; 4,822,543; 4,889,595; 4,889,597; 4,889,596; and 4,898,642.

The use of such fibers in combination with absorbent gelling materials, and means for manufacturing such combinations, are described in U.S. Pat. No. 4,935,022. Such preparations typically involve the use of aldehydes, such as glutaraldehyde, as crosslinking agents. In addition, polycarboxylic acids can be used as crosslinking agents. It will be appreciated that other means for preparing other crosslinked cellulosic fibers are also known, and such fibers may also be used herein, although the fluid absorbency properties may be suboptimal as compared with the above-mentioned fibers. Reference can be made to the various citations in U.S. Pat. No. 4,898,642 and PCT U.S. 89 01581 for other fiber types. Once in hand, the curled cellulosic fibers are refined to provide the fibers used to prepare the preferred absorbent cores used in the practice of this invention.

C. Backsheet

The backsheet 23 is impervious to liquids (e.g., menses and/or urine) and is preferably manufactured from a thin plastic film, although other flexible liquid impervious materials may also be used. As used herein, the term "flexible" refers to materials which are compliant and will readily conform to the general shape and contours of the human body. The backsheet 23 prevents the exudates absorbed and contained in the absorbent core 24 from wetting articles which contact the sanitary napkin 20 such as pants, pajamas and undergarments. The backsheet 23 may thus comprise a woven or nonwoven material, polymeric films such as thermoplastic films of polyethylene or polypropylene, or composite materials such as a film-coated nonwoven material. Preferably, the backsheet is a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P18-0401 and by Ethyl Corporation, Visqueen Division, of Terre Haute, Ind., under the designation XP-39385. The backsheet 23 is preferably embossed and/or matte finished to provide a more clothlike appearance. Further, the backsheet 23 may permit vapors to escape from the absorbent core 24 (i.e., breathable) while still preventing exudates from passing through the backsheet 23.

D. Flow Regulator

The flow regulator 21 may be any means which is capable of acquiring and distributing liquids (e.g., menses and/or urine). It is important that the flow regulator 21 maintain a proper balance in the movement of fluid in the longitudinal and z-directions. The flow regulator must be able to move the fluid substantially in the longitudinal direction prior to surrendering the fluid to the underlying absorbent core. By moving fluid substantially in the longitudinal direction the flow regulator provides a more effective use of the absorbent core. The flow regulator 21 preferably comprises a secondary topsheet 27 and a plurality of fibers having external intrafiber capillary channels 25.

(i) Secondary Topsheet

The secondary topsheet 27 may be any means which is capable of acquiring and distributing liquids (e.g., menses and/or urine). As shown in FIG. 2 the secondary topsheet 27 has a body surface, a garment surface, side edges and end edges. In addition the secondary topsheet 27 is gathered such that it provides a plurality of pleats 26 that extend substantially parallel to the longitudinal direction of the sanitary napkin 20. The secondary topsheet 27 helps to distribute and move fluid that has been deposited upon the topsheet 22. The secondary topsheet 27 may thus comprise a layer of material capable of being formed into pleats, and having interfiber capillaries such that fluid is transferred from the topsheet through to the core.

Preferably, the secondary topsheet 27 is a tissue having a basis weight of from about 0.025 g/in$^2$ to about 0.045 g/in$^2$ and a density of from about 0.06 to 0.11 g/cm$^3$. Exemplary tissues are manufactured by the Fort Howard corporation, Green Bay, Wisc.

(ii). The Capillary Channel Fibers

The sanitary napkin 20 preferably has a plurality of capillary channel fibers 25 that are positioned within the longitudinal pleats 26 of the secondary topsheet 27 and generally between the secondary topsheet 27 and the topsheet 22. Capillary channel fibers 25 are fibers having channels formed therein, preferably, on their exterior surfaces. FIGS. 3 to 7 show examples of some types of capillary channel fibers 25. Suitable capillary channel fibers are described below, and in the following Patent Applications which were filed on Jul. 23, 1991: U.S. patent applications Ser. No. 07/734,404 filed in the names of Thompson et al.; U.S. patent application Ser. No. 07/734,392 filed in the names Thompson et al.; and, U.S. patent application Ser. No. 07/734,405 filed in the names of Buenger et al. These patent applications may be referred to collectively as the "Capillary Channel Fiber" patent application. Suitable capillary channel fibers are also described in EPO Patent Application 0 391 814 published Oct. 10, 1990.

While a variety of capillary channel fibers can be used herein, the following description discusses some preferred characteristics of the capillary channel fiber 25 that are incorporated into the absorbent articles of this invention.

(a). Fiber Morphology

The capillary channel fibers 25, as noted above, have capillary channels 29 on their outer surfaces. The capillary channel fibers 25 are preferably bent or, most preferably, are in a curled configuration (that is, they are nonlinear). Most preferably, the capillary channel fibers 25 are "substantially curled" (or otherwise gathered). This provides the capillary channel fibers with a higher loft and increased resilience for a given number of fibers. By increasing the loft of the individual fibers, the overall loft of pads made therefrom is thicker and softer. This allows for the formation of low density, high loft pads which, assuming that the individual fibers themselves are not too thick or stiff are extremely comfortable, yet effective for transporting fluids.

However, the preferred nonlinear capillary channel fibers herein should not be "kinked". Kinking a capillary channel fiber can cause points of constriction of the capillary channels at each kinking site. This, of course, would interfere with fluid flow dynamics along the capillary channel.

Figure 8:
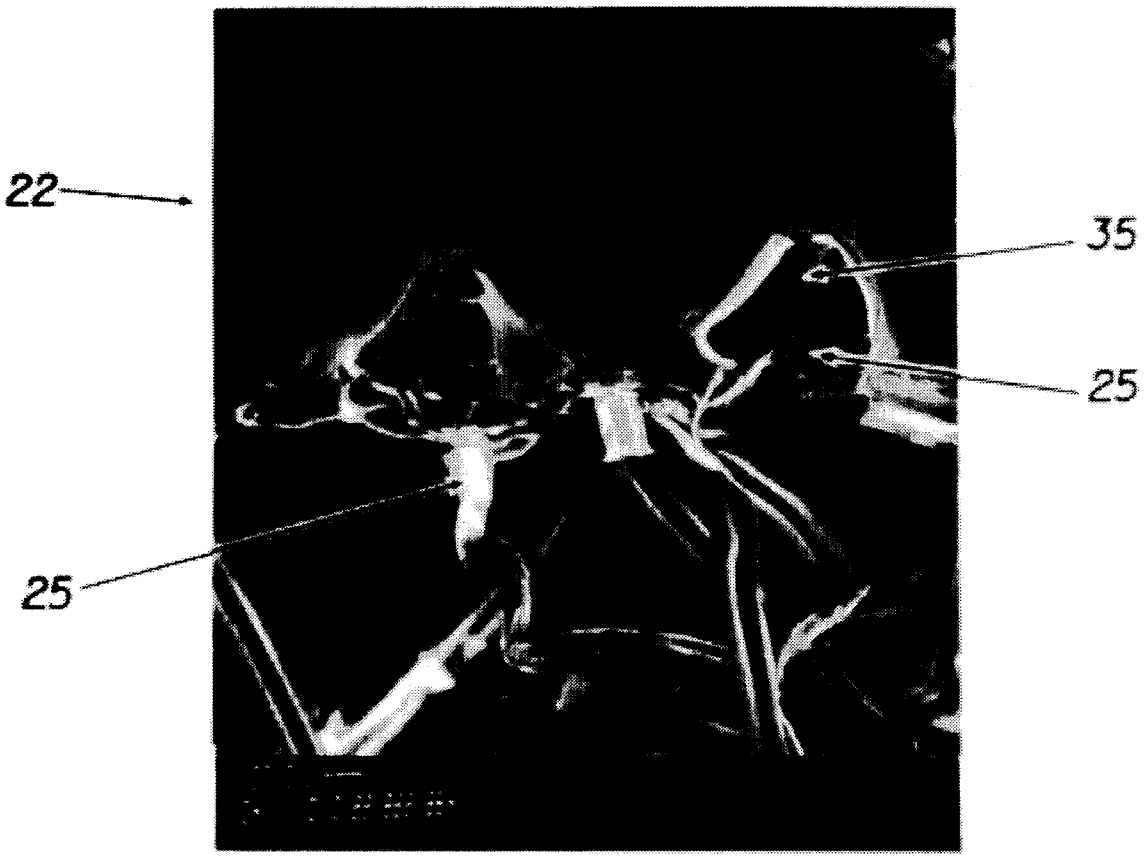
FIG. 8 is a photomicrograph sectional view taken of a sanitary napkin which shows the close contact between a formed film topsheet and an underlying layer of capillary channel fibers and the protrusion of capillary channel fibers into the pores of the topsheet.

In addition, there is another substantial advantage to employing nonlinear capillary channel fibers. As indicated in FIG. 8, it may be preferred that small portions, of the capillary channel fibers 25 actually protrude into at least some of the topsheet 22 orifices 35 of the articles herein. These protrusions are easier to effect when a capillary channel pad is prepared using curled capillary channel fibers. There is a greater likelihood that a number of ends and/or curls in the capillary channel fibers will find their way into the orifices of the topsheet material than if substantially linear capillary channels were to be employed. The capillary channel fibers 25 may be curled in a number of ways, including but not limited to: (1) selectively heat quenching the fibers as they come from their forming die by heating one side of the fibers a bit more than the other side (or, conversely, by cooling one side more quickly than the other); (2) fibers made from synthetic polymers such as polyesters can be curled by stretching, followed by relaxation, or by passing the fiber under tension around a sharp edge, followed by relaxation; or (3) by immersion in methanol. In a preferred mode, the fibers are substantially helical. Whatever means are used to crimp or otherwise curl the capillary channel fibers, they can, if desired, then be carded to form an assembly of fibers.

The preferred amplitude of the curls is in the range of about 0.1 mm to about 5 mm, and, typically, the frequency of the curls is from about 1 per inch of fiber to about 10 per inch of fiber. Fibers with amplitudes of about 0.5 mm and a frequency of about 6 crimps per inch exhibit good softness even in the higher denier ranged fibers having large capillary channels.

(b). Fiber Structure and Surface Properties

The capillary channel fibers 25 used herein can be prepared from any convenient polymer which is nonswelling when wet. Polymers such as polyethylene, polypropylene, polyesters (preferred), and the like, are useful herein, so long as they are spinnable such that they can be formed with external capillary channels, as noted hereinabove. Conveniently, the polymers are melt-extrudable. Typically, the capillary channel fibers herein will be prepared from a synthetic polyethylene terephthalate polymer melt having an inherent viscosity ("IV") of from about 0.6 to about 0.9. (IV is a term of art and can be determined in well-known fashion. See, for example, U.S. Pat. No. 4,829,761 at column 8.) The IV of a polymer melt bears some relationship to the ability of the polymer to retain the shape of the capillary channel walls, and is related to the average molecular weight of the polymers. For example, it is convenient to employ a polyester having an inherent viscosity of about 0.7 herein, but it would be more preferred to employ a polymer having an inherent viscosity of about 0.9, since this would allow the walls of the capillary channels to be thinner, yet sufficiently strong to avoid collapse under in-use pressure.

The capillary channel fibers 25 preferably have a denier of about 10 to about 22. However, it is to be understood that the denier of the fibers used is within the discretion of the formulator, and the denter per fiber can easily be in the range of about 25 to about 35.

The depth:width ratio of the capillary channels herein is preferably about 2.0, but processing restrictions, as noted above, as well as for economic reasons, a depth:width ratio of about 1.3 is typically employed. Typical and readily producible capillary channel fibers which are quite satisfactory for use herein thus have a depth-of-walls of about 46 microns and a width-between-walls of about 33 microns. The walls, themselves, are typically about 3–15 microns thick. Although variations in these dimensions are acceptable, capillary channel fibers prepared from polyester and having these characteristics are quite effective for their intended purpose. Such fibers can be prepared using conventional operating equipment and readily withstand pressures of the type encountered in sanitary devices, especially sanitary napkins and pantiliners, without collapse or spreading of the capillary channel walls to such an extent that their capillary function is lost.

The capillary channels 29 can be of various shapes. Certain shapes can offer particular advantages in particular product applications. For example, "U"-shaped, "H"-shaped, "C"-shaped with stabilizing legs depending therefrom and "V"-shaped capillary channels 25 may be used. Furthermore, the basic shapes may be repeated (see Figures), or even branched, to produce fibers containing multiple channels, but it will be appreciated that when more than about three repeating shapes are used, some additional stiffness may be noted in the fibers. The multiple "U" fibers of FIG. 6 offer the additional advantages of having additional capillarity due to face-to-fate contact and being easily curled.

The manufacture of capillary channel fibers 25 of the type employed herein is described in EPO Application 391,814 and in co-pending U.S. Continuation-In-Part Application entitled "Fibers Capable of Spontaneously Transporting Fluids", Ser. No. 07/736,261, filed Jul. 23, 1991, Inventors Phillips, Jones et al., Eastman Chemical Company; co-pending U.S. Patent Application entitled "Spinneret Orifices and Filament Cross-Sections with Stabilizing Legs Therefrom", Ser. No. 07/918,174, filed Jul. 23, 1992, Inventors Phillips, et al.; and in co-pending U.S. patent application entitled "Open Capillary Channel Structures, Improved Process for Making Capillary Channel Structures, and Extrusion Die for Use Therein", Ser. No. 07/482,446, filed Feb. 20, 1990, inventors Thompson and Krautter.

While the polymers used to prepare the capillary channel fibers herein are not, themselves, water-absorbent (nor are they absorbent to urine or blood-containing fluid such as menses), the fibers themselves are most preferably hydrophilic. Since most synthetic polymers are hydrophobic, the capillary channel fibers herein are surface-treated in order to render them hydrophilic.

The surface treatment of polymeric fibers involves processes which are well-known in the extensive fiber literature. In general, such processes involve treating the surface of the fibers with a "hydrophilizing agent", especially a surfactant. (Hydrophilization, which results in wettability of the fibers by aqueous fluids, can routinely be measured, for example, using contact angle measurements. In general, a contact angle less than 90° indicates a hydrophilic surface. A CAHN Surface Force Analyzer (SFA 222) can be used to measure hydrophilicity, as can a variety of other instruments known in the art.) Typical surfactant useful in such processes include various nonionic and anionic detersive surfactants of the general type known in the laundry literature. Hydrophilizing agents include wetting agents such as polyethylene glycol monolaurates (e.g., PEGOSPERSE 200ML, a polyethylene glycol 200 monolaurate available from Lonza, Inc., Williamsport, Pa,, USA), and ethoxylated oleyl alcohols (e.g., VOLPO-3, available from Croda, Inc., N.Y., New York, USA). Other types of hydrophilizing agents and techniques can also be used, including those well known to those skilled in the fiber and textile arts for increasing wicking performance, improving soil release properties, etc. Hydrophilizing agents can be added to the polymer at various stages prior to use, though preferably prior to drawing of the capillary channel fibers to their final size. For example, the hydrophilizing agent can be added in advance to the polymer prior to melting or blended into the polymer subsequent to melting. The additive hydrophilizing agent can also be applied to the polymer subsequent to formation, e.g., subsequent to exit from an extrusion die in a melt, wet, or dry spinning process, preferably prior to drawing of the fiber to small diameter. Of course, since the articles herein are intended to come into contact with sensitive regions of the human body, it is preferred that surfactants used to hydrophilize the surfaces of the capillary channel fibers be nontoxic and nonirritating to human skin. Various surfactant treatments for hydrophilizing the capillary channel fibers are described in the Examples hereinafter. Another method for hydrophilizing fibrous surfaces involves subjecting said surfaces to ionizing radiation, e.g., in a plasma, and such methods have the advantage that there is no surfactant residue on the surface of the fibers. Whatever the means, the overall objective is to secure capillary channel fibers for use herein which are spontaneously wettable by the fluids they are intended to transport.

(c). Various Forms of Capillary Channel Fibers

Preferably the capillary channel fibers 25 will be in the form of a yarn as illustrated in FIGS. 1 and 2. The yarn of capillary channel fibers 25 is comprised of individual capillary channel fibers 25 which have been gathered after spinning. Small twists in the yarn of capillary channel fibers 25 provides cohesiveness among the fibers.

Figure 3:
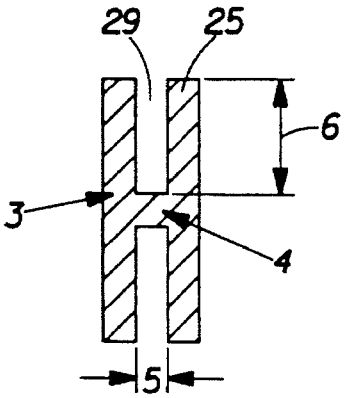
FIG. 3 is a cross-sectional view of a symmetrical "H"-shaped capillary channel fiber with a planar base (4), width between walls (5), and depth-of-walls (6)
Figure 4:
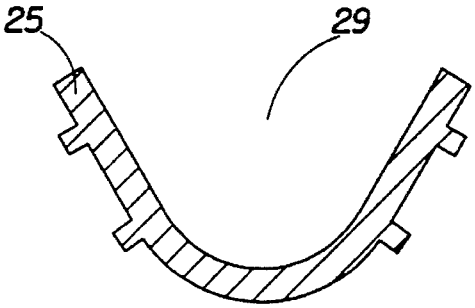
FIG. 4 is a cross-sectional view of a "C" shaped capillary channel fiber having stabilizing legs depending therefrom.
Figure 5:
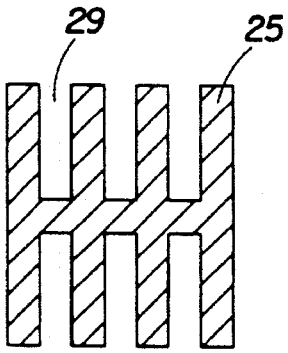
FIG. 5 is a cross-sectional view of a multiple "H"-shaped capillary fiber.
Figure 6:
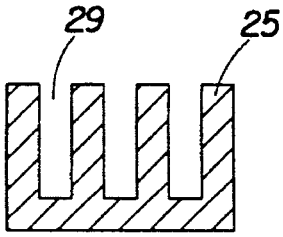
FIG. 6 is a cross-sectional view of a multiple "U"-shaped capillary channel fiber.
Figure 7A:
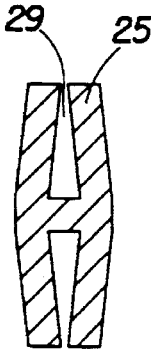
FIG. 7A is a cross-sectional view of an H-shaped capillary channel fiber in a partially collapsed state; (While not optimal, such fibers can be used herein)
Figure 7B:
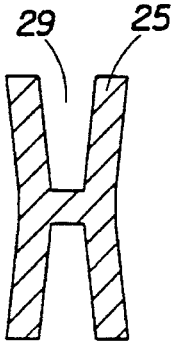
FIG. 7B is a cross-sectional view of an expanded capillary channel fiber.
Figure 7C:
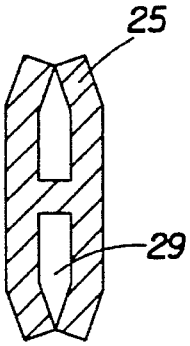
FIG. 7C is a cross-sectional view of a wholly collapsed capillary channel fiber; (Such fibers are not used herein)

The capillary channel fibers 25 used in the yarn preferably have an "H"-shaped cross-section as illustrated in FIGS. 3. The "H"-shaped capillary channel fibers 25 have a depth of walls of about 46 microns and a width between walls of about 33 microns. The fibers have a denier of about 16. The denier of the yarn of capillary channel fibers is about 657. The fibers are preferably helically curled and have an amplitude of about 0.15 mm and the frequency of the curls is about 8.3 per inch of fiber.

In another embodiment the capillary channel fibers 25 may be in the form of a nonwoven. The nonwoven is preferably a thermally bonded, rebulked and needled web comprised of 2 inch helically curled staple fibers. Other methods for forming the nonwoven include carding, rando process, spunbond, needlepunch, hydroentangled, and the like. The fibers have a denier per filament of about 17. The resultant nonwoven preferably has a basis weight of about 1.6 oz/yd$^2$. A suitable nonwoven comprised of capillary channel fibers is disclosed in U.S. Patent Application entitled "Fluid Accepting, Transporting, and Retaining Structure", Ser. No. filed Sep. 10, 1992, Inventors Thompson et al.

E. Fluid Flow Among the Various Layers

Initially fluid will impinge the topsheet 22 of the sanitary napkin 20. Fluid will then move through the topsheet 22 toward the flow regulator 21, which preferably comprises the secondary topsheet 27 and the yarn of capillary channel fibers 25. The flow regulator 21 which separates topsheet 22 from the absorbent core 24 prevents fluid from reaching the underlying absorbent core 24 too rapidly. As fluid contacts the yarn of capillary channel fibers 25 located within the pleats 26 of the secondary topsheet 27 fluid will be dispersed substantially in the longitudinal direction of the sanitary napkin 20. In other words, the flow regulator comprising the secondary topsheet 21 and the capillary channel fibers 25 facilitates longitudinal movement of the fluid rather than directly depositing the fluid onto the absorbent core 24 directly below the spot of impingement upon the topsheet 22.

The secondary topsheet 27 allows movement of fluid in the z-direction toward the absorbent core 24 but at such a rate that a substantial portion of the fluid is first moved longitudinally by the capillary channel fibers 25. Fluid is eventually allowed to penetrate the secondary topsheet 27 and is surrendered to the absorbent core 24.

By moving bodily fluids in the longitudinal direction prior to depositing them upon or relinquishing them to the absorbent core 24, better utilization of the absorbent core 24 is achieved. By better utilizing the entire absorbent core 24, side soiling can be reduced and for all practical purposes eliminated.

This concept of longitudinal movement of bodily fluids prior to relinquishing the fluids to the absorbent core 24 is particularly valuable in situations where, as in sanitary napkins, the target zone for bodily fluids is perhaps the narrowest portion of the sanitary napkin 20. Therefore, the human anatomy forces the largest capacity zones for the absorbent core to be in the transverse direction. Therefore, a vast majority of the absorbent core 24 is not utilized.

The overall movement of bodily fluids can be viewed as a z-direction movement and then a longitudinal movement followed by a z-direction movement. That is, as bodily fluids are deposited upon the sanitary napkin 20 they are first moved in the z-direction through the topsheet 22. Bodily fluids are then moved in the longitudinal direction by the flow regulator 21 before being surrendered to the underlying absorbent 24. As mentioned above, this allows the entire absorbent core 24 to be utilized more efficiently.

By moving fluids in the z-direction and then longitudinally followed by a z-direction movement, the capillary channel fibers 25 of the flow regulator 21 are "renewed" for the next infusion of fluid, thereby leaving the topsheet 22 with a fresh, dry appearance and feel. The sanitary napkin 20 is able to continue the process until the absorbent core 24 is saturated.

In order to move fluid among the various layers of the sanitary napkin 20 it is important that the various layers are kept in close or otherwise intimate contact with one another. This contact can be achieved by a number of suitable methods. These include but are not limited to bonding by adhesives, ultrasonics, and the like, or by tensional forces.

Thus, in a highly preferred mode there is an interconnecting network between topsheet 22, thence into the capillary channel fibers 25 and the secondary topsheet 27 of the flow regulator 21, and thence into the underlying absorbent core 24, whereby fluid efficiently proceeds through the topsheet 22, along the capillary channel fibers 25, into the secondary topsheet 27, and into the absorbent core 24. This interconnection between the various layers is maintained even in the face of in-use stresses such as moisture, mechanical shear, and pressure-relaxation associated with physical movement of the wearer.

If the adhesive attachment is used, several factors should be kept in mind. The amounts of the adhesive used in a pattern in which it is laid-down should minimize the sticking of the absorbent article to the user's body.

It will also be appreciated using excessive amounts of adhesives could undesirably clog the capillary channels in the fibers 25, thereby reducing their effectiveness. Accordingly, "noninterfering" amounts of adhesives are used. Such amounts can vary, depending on the adhesive chosen, the pattern in which it is laid down, the width of the capillary channels and the fibers, and the like. Controlling the amount of the adhesive also serves to minimize the sticking of the articles to the user's body.

The adhesive should be nonirritating to the skin and otherwise toxicologically-acceptable for use in close contact with delicate body tissues. The adhesive should maintain its bonding properties when moisture is not present, i.e., when the article is being manufactured, and most preferably, when moisture is present, i.e., when the article is being used.

The adhesive should bond both to the material used to manufacture the topsheet and to the material used to manufacture the capillary channel fibers. If the topsheet or the fibers are surfaced-treated, e.g., in a hydrophilization process, the nature of the surface treated will have be considered when selecting the adhesive.

Typical adhesives useful herein include materials selected from latex adhesives and hot melt adhesives.

The adhesive can be laid down in a random pattern, however, it is most preferred that a spiral, or multiple spiral, pattern, be used. The lines of adhesives are applied to the underside or garment side of the topsheet 22 in a spiral pattern using a 0.2 mm nozzle, but applications using nozzles at least as large as 0.6 mm are satisfactory. Alternatively, a spot pattern can be used to apply the adhesive to the topsheet 22, but is less preferred.

Suitable adhesives are available from Findley Adhesives, especially hot melt adhesives 4031, and latex 8085. The type of adhesive can vary somewhat depending on the type of finish present on the capillary channel fibers. Suitable finishes include Eastman's LK5483, LK5563 and most preferably Eastman's LK5570, as well as the polymer available as MILEASE T, which is well-known in the detergency arts (see, for example, U.S. Pat. No. 4,132,680) as a fiber-coating ethylene terephthalate/polyetholglycal terephthalate soil release polymer in which is available from ICI America.

The adhesives may be applied in an open pattern network of filaments of adhesives as disclosed in U.S. Pat. No. 4,573,986 issued to Minetola et al. on Mar. 4, 1986. Some suitable attachment means that utilize an open pattern network filaments comprising several lines of adhesive filaments is rolled into a spiral pattern art illustrated by the apparatus and methods disclosed in U.S. Pat. No. 3,911,173 issued to Sprague, Jr. on Oct. 7, 1975; U.S. Pat. No. 4,785,996 issued to Zieker et al. on Nov. 22, 1978; and U.S. Pat. No. 4,842,666 issued Werenicz on Jun. 27, 1989.

Close contact between the topsheet and the underlying layer of capillary channel fibers can be further improved by applying pressure during the gluing processing and/or by "combing" the uppermost capillary channel fibers to provide individual fibers protrusion which give better contact with the adhesive.

F. Optional Retaining Means

In use, the sanitary napkin 20 can be held in place by any support means or attachment means well-known for such purposes. Preferably, the sanitary napkin is placed in the user's undergarment or panty and secured thereto by a fastener such as an adhesive 36. The adhesive 36 provides a means for securing the sanitary napkin 20 in the crotch portion of the panty. Thus, a portion or all of the outer surface of the backsheet 23 is coated with adhesive. Any adhesive or glue used in the art for such purposes can be used for the adhesive herein, with pressure-sensitive adhesives being preferred. Suitable adhesives are Century A-305-IV manufactured by the Century Adhesives Corporation of Columbus, Ohio; and Instant Lock 34-2823 manufactured by the national Starch and Chemical Company of Bridgewater, N.J. Suitable adhesive fasteners are also described in U.S. Pat. No. 4,917,697. Before the sanitary napkin is placed in use, the pressure-sensitive adhesive 36 is typically covered with a removable release liner 37 in order to keep the adhesive 36 from drying out or adhering to a surface other than the crotch portion of the panty prior to use. Suitable release liners 37 are also described in the above-referenced U.S. Pat. No. 4,917,697. Any commercially available release liners commonly used for such purposes can be utilized herein. Non-limiting examples of suitable release liners are BL30MG-A Silox E1/0 and BL30MG-A Silox 4P/0 both of which are manufactured by the Akrosil Corporation of Menasha, Wis. The sanitary napkin 20 of the present invention is used by removing the release liner 37 and thereafter placing the sanitary napkin 20 in a panty so that the adhesive 36 contacts the panty. The adhesive 36 maintains the sanitary napkin in its position within the panty during use.

G. Optional Features

The sanitary napkin 20 may also be provided with two flaps 34, each of which are adjacent to and extend laterally from the side edge of the absorbent core. The flaps 34 are configured to drape over the edges of the wearer's panties in the crotch region so that the flaps 34 are disposed between the edges of the wearer's panties and the thighs.

The flaps 34 serve as least two purposes. First, the flaps 34 help serve to prevent swelling of the wearer's body and panties by menstral fluid, preferably by forming a double wall barrier along the edges of the panties. Second, the flaps 34 are preferably provided with attachment means on their garments surface so that the flaps 34 can be folded back under the panty and attached to garment facing side of the panty. In this way, the flaps 34 serve to keep the sanitary napkin 20 properly positioned in the panty.

The flaps 34 can be constructed of various materials including materials similar to the topsheet, backsheet, tissue, or combinations of these materials. Further, the flaps 34 may be a separate element attached to the main body portion of the napkin or can comprise extensions of the topsheet 22 and the backsheet 23 (i.e., unitary).

A number of sanitary napkins having flaps suitable or adaptable for use with the sanitary napkins of the present invention are disclosed in U.S. Pat. No. 4,687,478 entitled "Shaped Sanitary Napkin with Flaps", issued to Van Tilburg on Aug. 18, 1987; U.S. Pat. No. 4,589,876 entitled "Sanitary Napkin", issued to Van Tilburg on May 20, 1986; and U.S. Pat. No. 4,608,047, entitled "Sanitary Napkin Attachment Means", issued to Medingly on Aug. 26, 1986.

H. Assembly of the Components of a Sanitary Napkin

A sanitary napkin is preferably assembled in the following manner. For simplicity, the assembly is described in terms of one possible method. The steps described below can be carried out in many other orders. There are also numerous other ways to assemble the sanitary napkins. All such alternatives are within the scope of the present invention.

The secondary topsheet 27 is placed over a forming bar to form the first pleat in the secondary topsheet 27. This process is repeated until 6–12 pleats in all are formed in the secondary topsheet 27.

A yarn of capillary channel fibers 25 is then placed in each of the pleats 26 of the secondary topsheet 27. As can be seen some of the yarn of capillary channel fibers extends beyond the pleats of the secondary topsheet 27. The yarns of capillary channel fibers 25 may be placed in the pleats in a continuous strand, followed by snipping the yarn segments that extend beyond the ends of the secondary topsheet 27. Or alternatively, individual yarns precut to length may be placed within each pleat 26 of the secondary topsheet 27.

The underside of the topsheet 22 is then sprayed with an adhesive on its garment facing side. Preferably the adhesive is applied in spiral pattern to the garment side of the topsheet 22. The topsheet 22 is then placed on top of the pleated secondary topsheet 27 such that the capillary channel fibers 25 are positioned between the topsheet 22 and the secondary topsheet 27. Pressure is applied to achieve bonding.

Meanwhile the core 24 is secured to the body facing surface of the backsheet 23 using an adhesive. Prior to securing the core 24 to the backsheet 23 the components for the absorbent core 24 are obtained. The absorbent core 24 is preferably a laminate described above of two layers of cross-linked cellulosic fibers 41 and 42 with absorbent gelling particles 40 there between. The absorbent gelling material particles 40 are placed on top of the web (or bottom portion thereof) that will form the bottom layer 42 of cross-linked cellulosic fibers. The upper layer 41 of the core 24 is placed on top of the layered particles of absorbent gelling material 40. The components of the absorbent core are secured together by stitching or adhesive. The backsheet core assembly is then placed on the topsheet acquisition layer assembly which forms a preassembled sanitary napkin. The preassembled sanitary napkin is then ready to be sealed. The longitudinal side margins and end margins are then sealed. In a preferred process the longitudinal side margins and the end margins of the sanitary napkin are sealed by a heating element. The heating element is essentially used to "iron" the longitudinal side margins and the end margins together.

3. Alternative Embodiment of the Sanitary Napkin of the Present Invention

Figure 9:
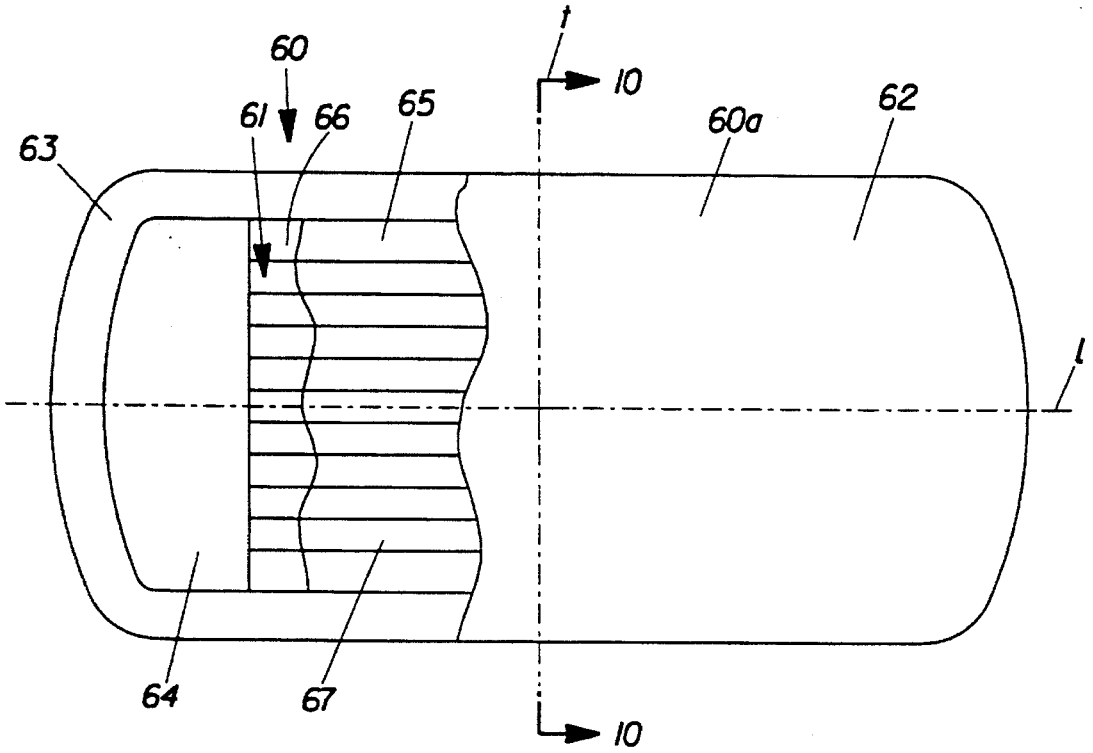
FIG. 9 is a top plan view of another embodiment of the sanitary napkin of the present invention with portions cut-away to more clearly show the construction of the sanitary napkin.

FIG. 9 is a top plan view of another embodiment of the sanitary napkin 60 of the present invention in its flat out state with portions of the structure being cut-away to more clearly show the construction of the sanitary napkin 60 and with the portion of the sanitary napkin 60 which faces or contacts the wearer 60*a*, oriented towards the viewer. As shown in FIG. 9, the sanitary napkin 60 preferably comprises a liquid pervious topsheet 62, a liquid impervious backsheet 63 joined with the topsheet 62, an absorbent core 64 positioned between the topsheet 62 and the backsheet 63, and flow regulator 61 positioned between the topsheet 62 and the absorbent core 64. The flow regulator 61 is comprised of a secondary topsheet 66 and a nonwoven 65 comprised of fibers having external capillary channels.

Figure 10:
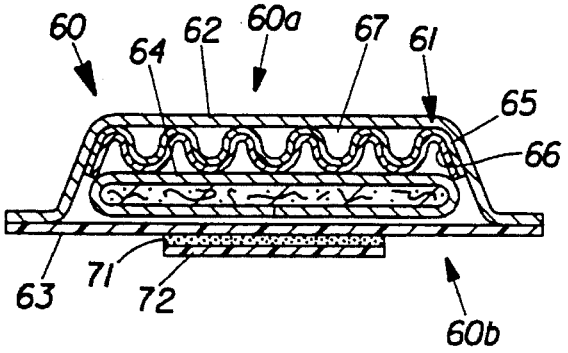
FIG. 10 is a cross-sectional view of the sanitary napkin of FIG. 9 taken along line 10—10.

FIG. 10 is a cross-sectional view of the sanitary napkin 60 taken along section line 10—10 of FIG. 9. As can be seen in FIG. 10 the nonwoven 65 comprised of fibers having external capillary channel fibers is superposed on the body facing surface of the secondary topsheet 66. Together, the secondary topsheet and the nonwoven form the flow regulator 61. The flow regulator 61 is preferably arranged to form a plurality of pleats 67 extending substantially parallel to the longitudinal direction of the sanitary napkin 60.

The sanitary napkin 60 has two surfaces, a body surface 60*a* and a garment surface 60*b*. A sanitary napkin 60 is shown in FIG. 9 as viewed from its body surface 60*a*. The body surface 60*a* is intended to be worn adjacent to the body of the wearer. The garment surface 60*b* of the sanitary napkin 60 (shown in FIG. 10) is on the opposite side and is intended to be placed adjacent to the wearer's undergarments when the sanitary napkin 60 is worn.

The sanitary napkin 60 preferably includes an adhesive fastening means 71 for attaching the sanitary napkin 60 to the undergarment of the wearer. Removable release liners 72 cover the adhesive fastening means 71 to keep the adhesive from sticking to a surface other than the crotch portion of the undergarment prior to use.

The backsheet 63, topsheet 62, core 64, adhesive 71 and release liner 72, secondary topsheet 66 and nonwoven 65 are preferably comprised of materials and constructions described more fully in detail above.

Preferably, the channels of the fibers of the nonwoven 65 are oriented substantially in the longitudinal direction. Thus, fluid deposited on the nonwoven 65 is moved in the longitudinal direction prior to being surrendered to the secondary topsheet 66, which surrenders it the absorbent core 64. This longitudinal fluid movement provides a more effective use of the absorbent core 64.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article having a longitudinal direction, a transverse direction, and a z-direction, said absorbent article comprising:

(a) a fluid pervious topsheet;

(b) a fluid impervious backsheet joined to said topsheet;

(c) an absorbent core positioned between said topsheet and said backsheet, said absorbent core having an uppermost surface facing said topsheet and a lowermost surface facing said backsheet; and (d) a flow regulator positioned between said topsheet and said absorbent core said flow regulator enhancing movement of fluid in the longitudinal direction while controlling movement of fluid in the transverse and z-directions.

2. The absorbent article according to claim 1 wherein said flow regulator comprises a secondary topsheet and a plurality of fibers having external capillary channels.

3. The absorbent article according to claim 2 wherein said secondary topsheet is arranged in a plurality of pleats extending substantially parallel to the longitudinal direction of said absorbent article.

4. The absorbent article according to claim 3 wherein said fibers having external capillary channels are formed into a yarn and positioned within the pleats of said secondary topsheet.

5. The absorbent article according to claim 3 wherein said fibers having external capillary channels are formed into a nonwoven web, said nonwoven web is superposed upon said secondary topsheet.

6. The absorbent article according to claim 5 wherein said fibers having external capillary channels of said nonwoven web are oriented such that their channels lie substantially parallel to the longitudinal direction of said article.

7. The absorbent article according to claim 2 wherein said fibers having external capillary channels are hydrophilic.

8. An absorbent article having a longitudinal direction, a transverse direction, and a z-direction, said absorbent article comprising:

(a) a liquid pervious topsheet;

(b) a liquid impervious backsheet joined to said topsheet;

(c) an absorbent core positioned between said topsheet and said backsheet, said absorbent core having an uppermost surface facing said topsheet and a lowermost surface facing said backsheet;

(d) a secondary topsheet positioned between said topsheet and said absorbent core, said secondary topsheet being arranged in a plurality of pleats extending substantially parallel to the longitudinal direction of said absorbent article; and (e) a plurality of fibers having external capillary channels being positioned between said topsheet and said secondary topsheet within said pleats of said secondary topsheet.

9. The absorbent article according to claim 8 wherein said fibers having external capillary channels are formed into a yarn.

10. The absorbent article according to claim 9 wherein the capillary channel fibers are hydrophilic.

11. The absorbent article according to claim 10 wherein the capillary channel fibers have a "H"-shaped cross-section.

12. The absorbent article according to claim 9 wherein the yarn of fibers having external capillary channels is twisted.

13. The absorbent article according to claim 8 wherein said absorbent core comprises absorbent gelling material disposed between the uppermost and lowermost surfaces of said core.

14. The absorbent article according to claim 8 wherein said secondary topsheet is a tissue.

15. An absorbent article having a longitudinal direction, a transverse direction, and a z-direction, said absorbent article comprising:

(a) a liquid pervious topsheet;

(b) a liquid impervious backsheet joined to said topsheet;

(c) an absorbent core positioned between said topsheet and said backsheet, said absorbent core having an uppermost surface facing said topsheet and a lowermost surface facing said backsheet;

(d) a secondary topsheet having a body facing surface and a garment facing surface positioned between said topsheet and said backsheet, said secondary topsheet being arranged in a plurality of pleats extending substantially parallel to the longitudinal direction of said absorbent article; and (e) a nonwoven web of fibers having external capillary channels being positioned between said topsheet and said secondary topsheet and being superposed on the body facing surface of said secondary topsheet.

16. The absorbent article according to claim 15 wherein said fibers having external capillary channels are oriented such that their channels lie substantially parallel to the longitudinal direction of said article.

17. The absorbent article according to claim 16 wherein said fibers having external capillary channels are hydrophilic.

18. The absorbent article according to claim 15 wherein said absorbent core comprises absorbent gelling material disposed between the uppermost and lowermost surfaces of said core.

19. The absorbent article according to claim 15 wherein said secondary topsheet is at issue.

* * * * *